(12) United States Patent
Onoe

(10) Patent No.: US 12,721,507 B2
(45) Date of Patent: Sep. 1, 2026

(54) ENDOSCOPE

(71) Applicant: OLYMPUS MEDICAL SYSTEMS CORP., Tokyo (JP)

(72) Inventor: Tomomichi Onoe, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 673 days.

(21) Appl. No.: 18/102,148

(22) Filed: Jan. 27, 2023

(65) Prior Publication Data

US 2023/0248230 A1 Aug. 10, 2023

Related U.S. Application Data

(60) Provisional application No. 63/307,720, filed on Feb. 8, 2022.

(51) Int. Cl.
*A61B 1/018* (2006.01)
*A61B 1/005* (2006.01)

(52) U.S. Cl.
CPC ............ *A61B 1/018* (2013.01); *A61B 1/0055* (2013.01)

(58) Field of Classification Search
CPC ...... A61B 1/018; A61B 1/0055; A61B 1/0008
See application file for complete search history.

(56) References Cited

U.S. PATENT DOCUMENTS 4,967,732 A * 11/1990 Inoue ................. A61B 1/00137 600/149
5,762,995 A * 6/1998 Kondo ............. A61M 25/0045 427/178
2011/0144429 A1* 6/2011 Finkman ................. A61B 1/12 600/156
2011/0313251 A1* 12/2011 Kitagawa ............ A61B 1/0055 600/142
2017/0095139 A1 4/2017 Yanagihara et al.
2018/0296288 A1 10/2018 Takahashi et al.
2019/0159659 A1 5/2019 Wakasone et al.

FOREIGN PATENT DOCUMENTS

JP 6017741 B1 11/2016
JP 6188995 B1 8/2017
JP 6720016 B2 7/2020
JP 6725688 B2 7/2020

* cited by examiner

*Primary Examiner* — Anh Tuan T Nguyen
*Assistant Examiner* — Rynae E Boler
(74) *Attorney, Agent, or Firm* — Morgan, Lewis & Bockius LLP

(57) ABSTRACT

An endoscope of the disclosure includes an insertion section including a conduit having an inner surface. The inner surface comprises a first projecting portion provided at a first position, and a second projecting portion provided at a second position. In a longitudinal direction of the insertion section, the first position is different from the second position.

13 Claims, 8 Drawing Sheets

10
11
Ax
2
9
33a
20
BIS
BIS
[3C]
[3C]
[3B]
[3B]
[3A]
[3A]
[3A]
[3A]
35b
36b
36a
35a
33
[4]
D2
D1
9
33a(33)
20
[3C]
9
33
20
33a
35b
36b
D4
[3B]
9
33
Ax
20
33a
36a
35a
D2
D3
[3A]

ENDOSCOPE

RELATED APPLICATION DATA

This application is based on and claims priority under 35 U.S.C. § 119 to U.S. Provisional Application No. 63/307,720 filed on Feb. 8, 2022, the entire contents of which are incorporated herein by reference.

FIELD OF THE DISCLOSURE

The present disclosure is related to an endoscope that may allow insertion of a treatment instrument through a conduit provided in an insertion section to perform a treatment, and may use the conduit as a suction conduit as well.

BACKGROUND

A treatment conventionally performed for a biological tissue using an endoscope inserted in a body cavity has been performed using a treatment instrument inserted through a treatment instrument insertion channel which is a conduit disposed by insertion through an insertion section of the endoscope. Examples of specific treatment include a resection treatment for a targeted biological tissue and a hemostatic treatment for a targeted bleeding site.

A conventional endoscope has a function of suctioning and removing blood or the like and residues or the like (including solidified blood, tissues, and the like; hereinafter referred to as suction targets) caused by bleeding or the like from a treatment target region or from the vicinity of the treatment target region. In this case, the treatment instrument insertion channel is used as a suction conduit as well.

In general, the blood and the like as suction targets have viscosity, and solidified residues or the like are included in the suction targets. A large suction force is therefore required in such a case of a procedure at the time of urgent bleeding or a procedure at the time of severe bleeding, for example. Thus, it is requested that a conventional endoscope that may use a treatment instrument insertion channel as a suction conduit as well should include a conduit having a larger diameter so as to ensure a high suction force for suction targets.

On the other hand, when allowing insertion of a treatment instrument through a conduit (treatment instrument insertion channel) to perform a predetermined treatment, a large gap is created between the conduit and the treatment instrument if the inner diameter of the conduit is large as compared with the maximum outer diameter of the treatment instrument. In this case, when allowing insertion of the treatment instrument through the conduit, the treatment instrument may not be allowed to advance in the conduit in a stable state.

The operability of the treatment instrument may be affected by a reason such as flection of the treatment instrument in a gap region in the conduit, for example. When the treatment instrument reaches a distal end side opening of the conduit, the treatment instrument may be moved in the radial direction in the gap region between the treatment instrument and the conduit to cause misalignment. This may result in a failure to stably hold the treatment instrument. In such a case, execution of a treatment through use of the treatment instrument may be affected. Thus, for conventional endoscopes, Japanese Patent No. 6720016, Japanese Patent No. 6188995, and Japanese Patent No. 6017741, for example, variously disclose proposals for an endoscope that may ensure good operability of a treatment instrument by including a configuration in which projecting portions or the like are provided on an inner surface of a conduit through which the treatment instrument is inserted or an outer circumferential surface of the treatment instrument to restrict radial movements of the treatment instrument in the conduit.

SUMMARY OF THE DISCLOSURE

An endoscope of an aspect of the present disclosure includes an insertion section including a conduit having an inner surface. The inner surface comprises a first projecting portion provided at a first position, and a second projecting portion provided at a second position. In a longitudinal direction of the insertion section, the first position is different from the second position.

An endoscope of an aspect of the present disclosure includes an insertion section; and a conduit provided in the insertion section. The conduit has an inner surface comprising a first projecting portion provided at a first position, and a first recessed portion provided a second position. With respect to a longitudinal axis of the insertion section, the first position is on an opposite side of the longitudinal axis from the second position.

DETAILED DESCRIPTION

In general, in a case of adopting a configuration in which projecting portions are provided on an inner surface of a conduit, for example, to restrict radial movements of a treatment instrument inserted through the conduit, the inner diameter of the conduit is partially reduced. In this case, a problem arises in that a suction force is reduced when the conduit is used as a suction conduit.

An embodiment of the present disclosure which will be described below can provide an endoscope including a conduit having a large diameter in an insertion section, in which insertion and holding of a treatment instrument inserted through the conduit are stably performed to ensure operability of the treatment instrument, and the suction force is prevented from being reduced.

Hereinafter, the present disclosure will be described with reference to an illustrated embodiment. Note that each drawing as referred to in the following description is schematically shown, and the dimensional relationship among respective members, scale, and the like may be shown differently for each of constitutional elements in order to show each of the constitutional elements with a size enough to be recognized on the drawings. Therefore, the present disclosure is not limited to illustrated forms alone in terms of the number of each of the constitutional elements depicted, the shape of each of the constitutional elements, the size ratio of the respective constitutional elements, the relative positional relationship among the respective constitutional elements, and the like in the respective drawings.

Figure 1:
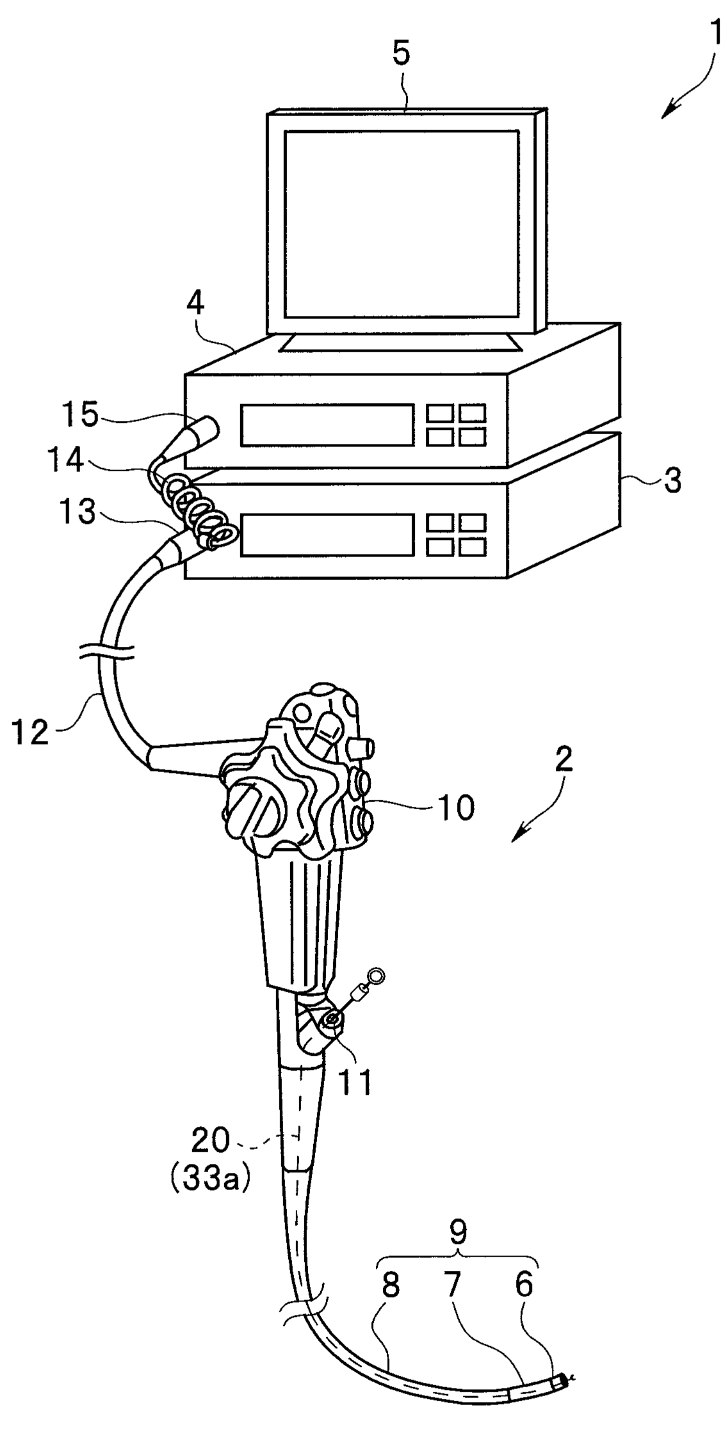
FIG. 1 is a schematic perspective view showing an entire endoscope system including an endoscope of an embodiment of the present disclosure.
Figure 2:
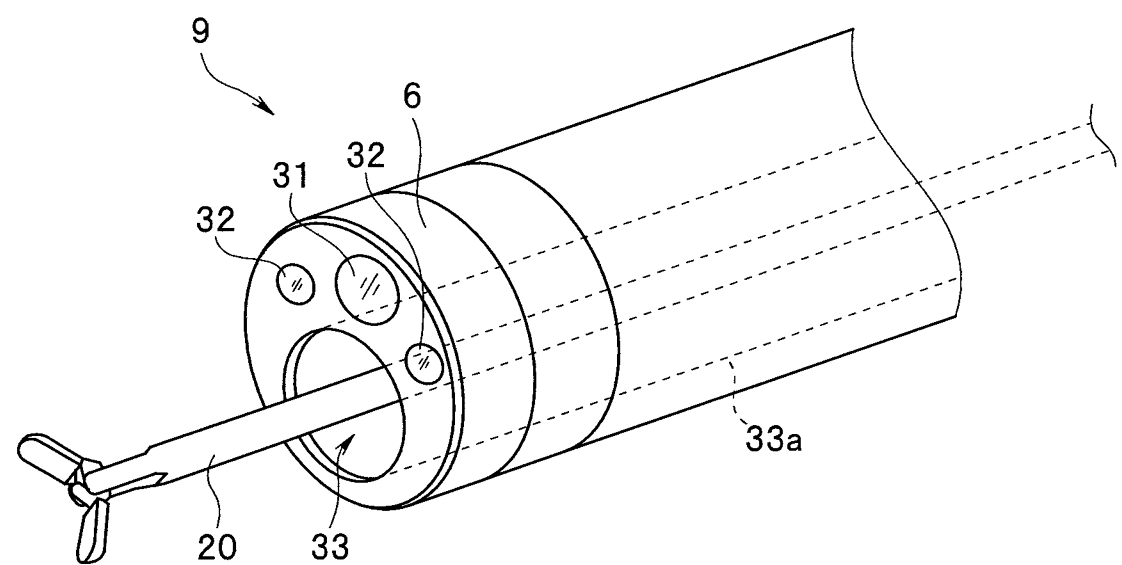
FIG. 2 is a main part enlarged perspective view showing the vicinity of a distal end portion of an insertion section of the endoscope of the embodiment of the present disclosure in an enlarged manner.

First, an overview of an entire configuration of an endoscope system including an endoscope of an embodiment of the present disclosure will be described below with reference to FIG. 1 and FIG. 2. FIG. 1 is a schematic perspective view showing the entire endoscope system including the endoscope of the embodiment of the present disclosure. FIG. 2 is a main part enlarged perspective view showing the vicinity of a distal end portion of an insertion section of the endoscope of the embodiment of the present disclosure in an enlarged manner.

As shown in FIG. 1, an endoscope system 1 including an endoscope 2 of the present embodiment is composed of the endoscope 2, a light source device 3, a video processor 4, a display device 5, a treatment instrument 20, and the like.

The endoscope 2 is composed of an insertion section 9 having a substantially elongated tube shape, an operation section 10, a universal cord 12, and the like.

The insertion section 9 is formed by a distal end portion 6, a bending portion 7, and a flexible tube portion 8 provided continuously in order from a distal end side. The insertion section 9 is thus formed into a substantially elongated tube shape as a whole. The operation section 10 is connected to a proximal end portion of the insertion section 9.

The insertion section 9 is configured by integrally forming a conduit 33*a* and the like using a multi-lumen tube, for example. In the case of the configuration, the insertion section 9 has the distal end portion 6 provided continuously to the distal end side of the multi-lumen tube. The conduit 33*a* integrally formed on the multi-lumen tube side is coupled to a conduit formed in the distal end portion 6. The conduit in the distal end portion 6 is open in a distal end surface (a channel opening 33 which will be described later). Therefore, the conduit 33*a* as referred to in the following description will indicate not only the conduit 33*a* integrally formed on the multi-lumen tube side, but also a conduit leading to the opening (33) in the distal end surface of the distal end portion 6. The endoscope 2 comprises an insertion section 9 including the conduit 33*a* having an inner surface. The inner surface comprises a first projecting portion 35*a* provided at a first position, and a second projecting portion 24*b* provided at a second position. In a longitudinal direction of the insertion section 9, the first position is different from the second position. In a circumferential direction of the insertion section 9, the first position is different from the second position. The first projecting portion 35*a* is provided on a first inner surface portion and the second projecting portion 35*b* is provided on a second inner surface portion. In a side cross-sectional view, the first inner surface portion is on a first side of a longitudinal axis of the insertion section 9 and the second inner surface portion is on a second side of the longitudinal axis of the insertion section 9. The first projecting portion and the second projecting portion may be provided at a distal end side of the insertion section.

Note that examples of the configuration of the insertion section 9 may include a form in which a separate channel tube (the conduit 33*a*), a signal transmission cable which will be described later, and the like are inserted through and arranged in a tube-like member, in addition to the above-described form. Also in the case of the configuration, the channel tube as the conduit 33*a* is coupled to the conduit in the distal end portion 6. Therefore, the conduit 33*a* also includes the conduit leading to the opening (33) in the distal end surface of the distal end portion 6 similarly to the above-described configuration.

Inside the insertion section 9, the conduit 33*a* inserted through in a direction of a longitudinal axis from the proximal end to the distal end is provided. The conduit 33*a* is a treatment instrument insertion channel through which the treatment instrument 20 is inserted, and also serves as a suction conduit when suction targets in a body cavity are suctioned.

Units such as an image pickup unit and an illumination unit, neither shown, are provided inside the distal end portion 6. Thus, as shown in FIG. 2, for example, an observation window 31, (two) illumination windows 32, the channel opening 33, and the like are provided in the distal end surface of the distal end portion 6 of the insertion section 9.

The observation window 31 is a light-transmissive optical member that constitutes part of an observation optical system (not shown). The observation optical system is a constituent member having a function of forming an optical image of an observation target. Although illustration is omitted, an image pickup unit including an image pickup device and a driving circuit for the image pickup device, a signal processing circuit, and the like is disposed behind the observation optical system.

The illumination windows 32 are light-transmissive optical members that constitute part of an illumination optical system and an illumination device (neither shown). The illumination windows 32 are constituent members having a function of emitting light fluxes transferred from the light source device 3 toward an observation target in front of the distal end portion 6. Note that for the endoscope 2 of the present embodiment, a configuration example in which the illumination windows 32 are provided at respective positions substantially facing each other across the observation window 31 is shown.

The channel opening 33 is a distal end side opening of the treatment instrument insertion channel (the conduit 33*a*), and also serves as a distal end side opening of the suction conduit.

FIG. 2 shows a state in which a distal end of the treatment instrument 20 inserted through and arranged in the treatment instrument insertion channel protrudes forward from the channel opening 33. A treatment for a treatment target region to be performed by inserting the insertion section 9 of the endoscope 2 in a body cavity and using the treatment instrument 20 inserted through the treatment instrument insertion channel of the insertion section 9 is performed in a state as shown in FIG. 2.

Note that the internal configuration of the distal end portion 6 has a configuration substantially the same as the internal configuration of a distal end portion of a conventional endoscope. Therefore, detailed description and illustration of the internal configuration of the distal end portion 6 except the constituent members described above are omitted.

Examples of the treatment instrument 20 inserted through the treatment instrument insertion channel include treatment instruments of various forms formed by providing tools, such as a needle and a wire, suitable for various applications at the distal end, in addition to the treatment instrument in the form shown in FIG. 2 (the form in which a forceps is provided at the distal end).

The operation section 10 is configured to have an operation section main body, a plurality of operation members, a forceps opening 11, and the like. The operation section main body has a substantially box-like shape as a whole, and constitutes a grasping section. The insertion section 9 is extended from the operation section main body as described above. The plurality of operation members are operation members for performing various operations of the endoscope 2. These plurality of operation members are provided at predetermined positions on an external surface of the operation section main body.

The forceps opening 11 is provided at a predetermined position of the operation section main body of the operation section 10. The forceps opening 11 is a proximal end side opening when allowing insertion of the treatment instrument 20 of a predetermined form through the conduit 33*a* (the treatment instrument insertion channel) provided in the insertion section 9 of the endoscope 2.

The universal cord 12 is a tube-like member that extends from a side of the operation section 10. A scope connector 13 is provided at a distal end of the universal cord 12. The scope connector 13 is connected to the light source device 3.

The light source device 3 is a device that supplies illumination light for the illumination optical system and the illumination device (neither shown) provided inside the distal end portion 6 of the insertion section 9 of the endoscope 2. Illumination light radiated from the light source device 3 is transferred from the light source device 3 to the distal end portion 6 of the insertion section 9 of the endoscope 2 through an optical fiber cable or the like (not shown) inserted through and arranged in the scope connector 13, the universal cord 12, the operation section 10, and the insertion section 9. The illumination light then passes through the illumination windows 32 (see FIG. 2) provided in the front surface of the distal end portion 6 to be emitted toward an observation target in front of the distal end portion 6.

Note that although the configuration in which illumination light from the light source device 3 is transferred to the distal end portion 6 through the optical fiber cable or the like is illustrated as the illumination device, the present disclosure is not limited to the configuration. A configuration may be adopted in which an LED (light emitting diode) or the like as an illumination light source, for example, is provided inside the distal end portion 6, and light emission control over the illumination light source (LED) is exerted by the light source device 3.

A scope cable 14 extends laterally from the scope connector 13. An electric connector unit 15 is provided at a distal end of the scope cable 14. The electric connector unit 15 is connected to the video processor 4.

The video processor 4 is a control device that controls the present endoscope system 1 as a whole. In this case, the video processor 4 includes circuits such as a signal processing circuit that receives an image pickup signal from the image pickup unit (not shown) provided inside the distal end portion 6 of the insertion section 9 of the endoscope 2 to perform predetermined signal processing and a control processing circuit that outputs, for example, a control signal for driving the image pickup unit.

The video processor 4 and the image pickup unit are electrically connected with a signal transmission cable (not shown). Thus, the signal transmission cable is inserted through and arranged in the electric connector unit 15, the universal cord 12, the operation section 10, and the distal end portion 6 of the insertion section 9. This configuration enables the image pickup signal outputted from the image pickup unit, the control signal outputted from the video processor 4, and the like to be transferred between the image pickup unit and the video processor 4 through the signal transmission cable. Note that a composite cable in a form in which a plurality of cables are bundled and covered by a sheath shield, a sheath tube, or the like is applied, for example, as a form of the signal transmission cable.

The video processor 4 and the display device 5 are connected using a video cable (not shown). The video cable transmits an image signal, a control signal, and the like outputted from the video processor 4 to the display device 5.

The display device 5 receives the image signal and the control signal outputted from the video processor 4, and performs, for example, display of an endoscope image and various types of information in a predetermined form in accordance with the received control signal.

In the endoscope 2 of the present embodiment included in the endoscope system 1 configured in this manner, the conduit 33*a* to be used both as the treatment instrument insertion channel and the suction conduit is provided inside the insertion section 9, as described above. Herein, the configuration of the conduit 33*a* provided in the insertion section 9 of the endoscope 2 of the present embodiment will be described in detail with reference to FIG. 3 and FIG. 4.

Figure 3:
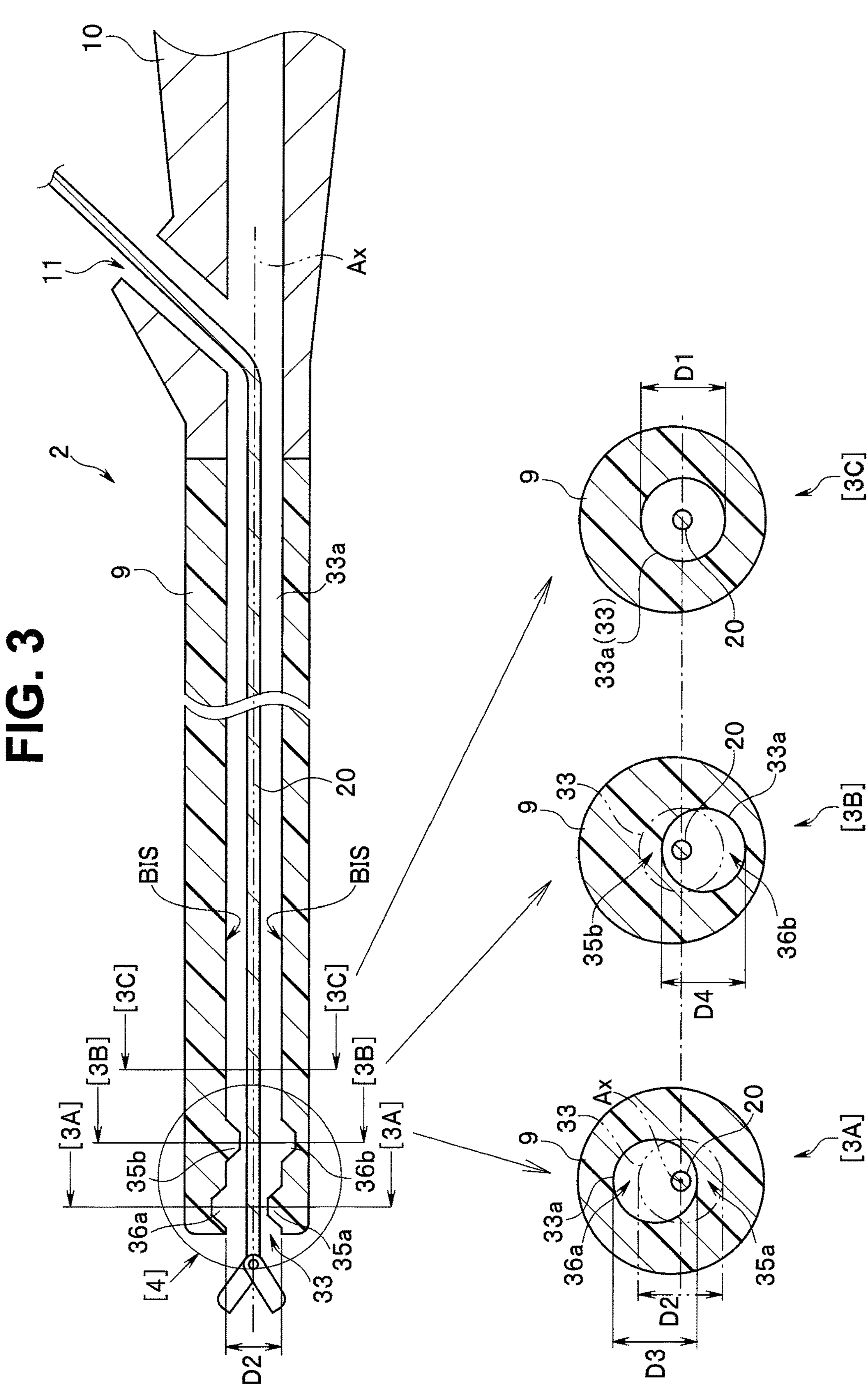
FIG. 3 is a cross-sectional view conceptually showing a configuration of a conduit provided in the insertion section of the endoscope of the embodiment of the present disclosure.
Figure 4:
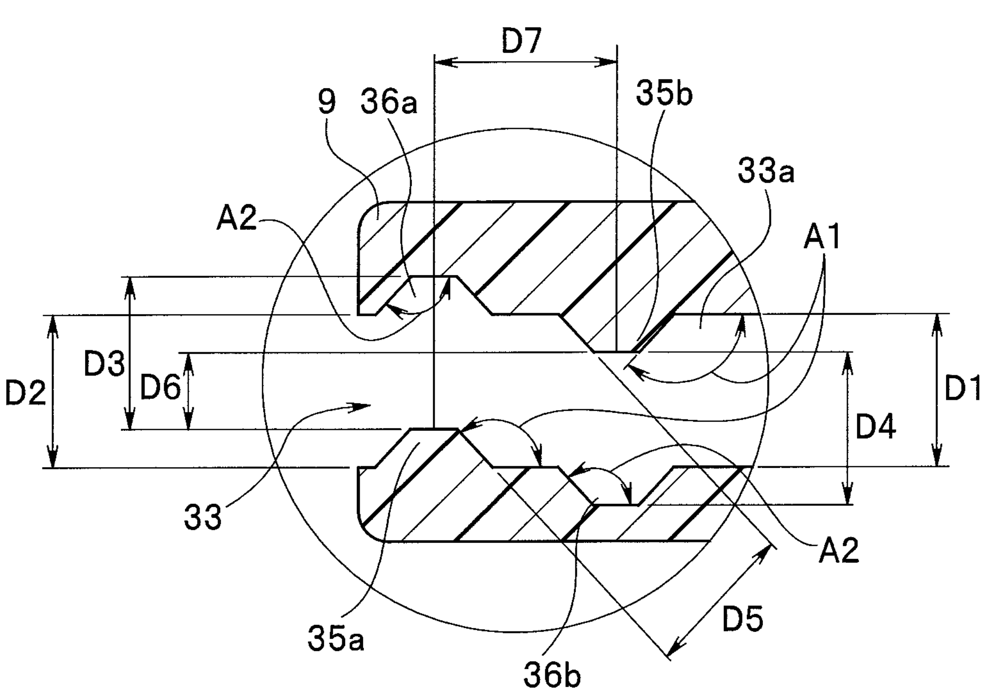
FIG. 4 is a main part enlarged cross-sectional view showing a portion indicated by a reference character [4] in FIG. 3 in an enlarged manner.

FIG. 3 is a cross-sectional view conceptually showing a configuration of the conduit provided in the insertion section of the endoscope of the present embodiment. FIG. 4 is a main part enlarged cross-sectional view showing a portion indicated by a reference character [4] in FIG. 3 in an enlarged manner. Note that in FIG. 3, a reference character [3A] indicates a cross-section taken along the line [3A]-[3A] in FIG. 3. In FIG. 3, a reference character [3B] indicates a cross-section taken along the line [3B]-[3B] in FIG. 3. Similarly, in FIG. 3, a reference character [3C] indicates a cross-section taken along the line [3C]-[3C] in FIG. 3. In FIG. 3 and FIG. 4, mainly paying attention to the conduit alone, the configuration of the conduit is conceptually shown. Therefore, in FIG. 3 and FIG. 4, illustration of the remaining constituent members other than the conduit in the insertion section of the endoscope of the present embodiment is omitted.

As shown in FIG. 3 and FIG. 4, the conduit 33*a* provided in the insertion section 9 is configured by providing a plurality of projecting portions that protrude toward the inner side of the conduit 33*a* on the inner surface at least in the vicinity of the distal end portion of the insertion section 9.

Herein, the configuration example shown in FIG. 3 and FIG. 4 shows a configuration example in which two projecting portions of a first projecting portion 35*a* and a second projecting portion 35*b* are provided, for example. In addition, the configuration example shown in FIG. 3 and FIG. 4 is shown assuming a configuration configured using a multi-lumen tube, for example, as the insertion section 9 and applied to what is called a single-use endoscope. Note that the configuration of the present disclosure is not limited to the illustrated configuration example, and can similarly be applied to what is called a reuse endoscope in a form that can be repeatedly used by being subjected to a cleaning and sterilization operation after use, for example.

Describing in detail, the first projecting portion 35*a* and the second projecting portion 35*b* are both provided on the inner surface of the conduit 33*a* as shown in FIG. 3 and FIG. 4. In this case, the second projecting portion 35*b* is provided at a position different from a first position (see the position indicated by the reference character [3A] in FIG. 3) at which the first projecting portion 35*a* is provided in a direction along a central axis Ax extending in the longitudinal direction of the conduit 33*a* and at a position different from the first position of the first projecting portion 35*a* in the circumferential direction around the central axis Ax of the conduit 33*a*. Herein, the position at which the second projecting portion 35*b* is provided is called a second position (see the position indicated by the reference character [3B] in FIG. 3). A position different from the first position and the second position on the inner surface of the conduit 33*a* is called a third position (see the position indicated by the reference character [3C] in FIG. 3).

In other words, the second projecting portion 35*b* is provided at a position away from the first position of the first projecting portion 35*a* by a predetermined distance (see a reference character D7 in FIG. 4) toward the proximal end in the direction along the longitudinal axis extending in the longitudinal direction of the insertion section 9 (the conduit 33*a*) and at a position away from the first position of the first projecting portion 35*a* by a predetermined rotation angle (substantially 180 degrees) in the circumferential direction around the central axis Ax of the conduit 33*a*. In other words, the first projecting portion 35*a* and the second projecting portion 35*b* are provided at positions axially symmetric to each other around the central axis Ax of the conduit 33*a*.

In addition, a first recessed portion 36*a* is formed at a position (surface) substantially facing the first projecting portion 35*a* on the inner surface of the conduit 33*a*. Similarly, a second recessed portion 36*b* is formed at a position (surface) substantially facing the second projecting portion 35*b* on the inner surface of the conduit 33*a*. The inner surface comprises a first recessed portion, a second recessed portion 36*b* at the second position. The first recessed portion 36*a* is on the second side of the longitudinal axis of the insertion section 9 and facing the first projecting portion 35*a*. The first projecting portion 35*a* includes a first projecting side wall surface. The first recessed portion 36*a* includes a first recessed side wall surface and a bottom surface. The first projecting side wall surface intersects a baseline surface BIS of the conduit 33*a* at an obtuse angle A1. The first recessed side wall surface intersects the bottom surface at an obtuse angle A2. The first recessed portion 36*a* faces the first projecting portion 35*a* and the second recessed portion 36*b* faces the second projecting portion 35*b*.

In this case, the height dimension of each of the first projecting portion 35*a* and the second projecting portion 35*b* and the depth dimension of each of the first recessed portion 36*a* and the second recessed portion 36*b* are set to be substantially identical. This configuration makes the inner diameter of the conduit 33*a* (the inner diameter in a plane perpendicular to the longitudinal direction) substantially identical at the first position of the first projecting portion 35*a*, the second position of the second projecting portion 35*b*, and the third position.

In this manner, the first projecting portion 35*a*, the second projecting portion 35*b*, the first recessed portion 36*a*, and the second recessed portion 36*b* are provided at predetermined positions on the inner surface of the conduit 33*a*. This configuration ensures an always substantially constant inner diameter (the inner diameter in a plane perpendicular to the longitudinal direction) for the conduit 33*a*.

Herein, in FIG. 3 and FIG. 4, a reference character D1 indicates the inner diameter of the conduit 33*a* in the plane perpendicular to the longitudinal direction at the third position of the inner surface of the conduit 33*a*. A reference character D2 (an alternate long and two short dashes line) indicates the position of the channel opening 33 when the distal end of the insertion section 9 is seen from the front surface. A reference character D3 indicates the inner diameter of the conduit 33*a* in the plane perpendicular to the longitudinal direction at the first position of the first projecting portion 35*a*. A reference character D4 indicates the inner diameter of the conduit 33*a* in the plane perpendicular to the longitudinal direction at the second position of the second projecting portion 35*b*. The first projecting portion 35*a* has a first height in a radial direction of the conduit 33*a*. The second projecting portion 35*b* has a second height in the radial direction of the conduit 33*a*. The first height and the second height are less than a radius of the conduit 33*a*. A shortest distance D5 is between the first projecting portion 35*a* and the second projecting portion 35*b*, the shortest distance is larger than an inner diameter D2 of the conduit 33*a*.

Therefore, in this case, the inner diameter at each part of the conduit 33*a* in the plane perpendicular to the longitudinal direction is set at

D1≈D2≈D3≈CD4.

In the endoscope 2 of the present embodiment, the configuration prevents the suction force when suction targets are suctioned using the conduit 33*a* as the suction conduit from being reduced.

In FIG. 4, a reference character D6 indicates a spaced distance (interval) between the top part of the first projecting portion 35*a* and the top part of the second projecting portion 35*b* in the plane perpendicular to the longitudinal direction. Herein, the top part of the first projecting portion 35*a* and the top part of the second projecting portion 35*b* are formed at the spaced distance (interval) D6 which is larger than or equal to the maximum outer diameter of the treatment instrument 20 inserted in the conduit 33*a* in the direction perpendicular to the longitudinal axis. This configuration may enable the treatment instrument 20 to be inserted through the conduit 33*a* and arranged at the position protruding forward from the channel opening 33.

Note that in this case, the spaced distance (interval) D6 between the top part of the first projecting portion 35*a* and the top part of the second projecting portion 35*b* is set at approximately 2.8 mm to 3.2 mm, for example, considering the maximum outer diameter dimension of the treatment instrument 20. This value setting enables the treatment instrument 20 to be stably inserted through the conduit 33*a*.

In this manner, the two projecting portions (35*a*, 35*b*) are formed such that the distance (interval) D6 more than or equal to the maximum outer diameter of the treatment instrument 20 is ensured, and predetermined set values are obtained as appropriate. This configuration enables the treatment instrument 20 to be stably held by the two projecting portions (35*a*, 35*b*) in a case of performing a predetermined treatment using the treatment instrument 20 in a state where the treatment instrument 20 is caused to protrude forward relative to the distal end surface of the distal end portion 6 of the insertion section 9.

In FIG. 4, a reference character D5 indicates the shortest distance between the first projecting portion 35*a* and the second projecting portion 35*b* (the inner diameter of a meandering portion of the conduit 33*a*). Herein, it may be configurated that the shortest distance D5 between the two projecting portions (35*a*, 35*b*) are set at least at a diameter substantially identical to the inner diameter D1 of the conduit 33*a* at the third position or a diameter larger than the inner diameter D1 (D5≥D1).

In this case, it is known that the shortest distance D5 between the two projecting portions (35*a*, 35*b*) varies in accordance with the spaced distance (interval) D7 between the first projecting portion 35*a* and the second projecting portion 35*b* in the longitudinal direction. Therefore, in order to set the shortest distance D5 between the two projecting portions (35*a*, 35*b*), the spaced distance D7 between the two projecting portions (35*a*, 35*b*) in the longitudinal direction should be set as appropriate.

In other words, if the spaced distance D7 between the two projecting portions (35*a*, 35*b*) in the longitudinal direction is set to be large, the shortest distance D5 can be set to be large. However, if the spaced distance D7 is excessively large, stable holding of the treatment instrument 20 by the two projecting portions (35*a*, 35*b*) may be affected. It can be therefore to set the shortest distance D5 to be substantially equal to the inner diameter D1 at the third position.

Further, it can be to form the two projecting portions (35*a*, 35*b*) such that an angle of portions indicated by the reference character A1 in FIG. 4 is an obtuse angle. This configuration enables the treatment instrument 20 inserted through the conduit 33*a* to be smoothly inserted through the conduit 33*a* without being caught by the two projecting portions (35*a*, 35*b*) when advancing from the proximal end side toward the distal end side.

Furthermore, in addition to the configuration (the configuration in which the angle A1=an obtuse angle), it can be to form the two recessed portions (36*a*, 36*b*) such that an angle of portions indicated by the reference character A2 in FIG. 4 is an obtuse angle. This configuration enables insertion of the treatment instrument 20 through the conduit 33*a* to be more smoothly performed.

In other words, the treatment instrument 20 which advances in the conduit 33*a* from the proximal end side toward the distal end side comes into contact with the sloping surface (obtuse angle) of the second projecting portion 35*b*, and the traveling direction is slightly changed. This allows the treatment instrument 20 to smoothly travel in the conduit 33*a* without being caught by the second projecting portion 35*b*. At this time, the treatment instrument 20 moves slightly in a direction toward the second recessed portion 36*b*. However, the traveling direction of the treatment instrument 20 is slightly changed by coming into contact with the sloping surface (obtuse angle) of the second recessed portion 36*b*. This allows the treatment instrument 20 to smoothly travel in the conduit 33*a* without being caught by the second recessed portion 36*b*. At this time, the treatment instrument 20 moves slightly in a direction toward the first projecting portion 35*a*.

The treatment instrument 20 then comes into contact with the sloping surface (obtuse angle) of the first projecting portion 35*a*, and the traveling direction is slightly changed similarly. This allows the treatment instrument 20 to smoothly travel in the conduit 33*a* without being caught by the first projecting portion 35*a*. At this time, the treatment instrument 20 moves in a direction toward the first recessed portion 36*a*. The traveling direction of the treatment instrument 20 is then slightly changed at the sloping surface (obtuse angle) of the first recessed portion 36*a*. This allows the treatment instrument 20 to smoothly travel in the conduit 33*a* without being caught by the first recessed portion 36*a*. The treatment instrument 20 then moves in a direction toward the channel opening 33.

Thus, when the treatment instrument 20 is brought into the state protruding forward from the distal end surface of the insertion section 9, the treatment instrument 20 is in the state inserted through the conduit 33*a*. At this time, in the vicinity of the distal end portion of the insertion section 9, the treatment instrument 20 is stably held between the top part of the first projecting portion 35*a* and the top part of the second projecting portion 35*b* (see the reference character D6 in FIG. 4).

Therefore, the configuration of the present embodiment may enable insertion of the treatment instrument 20 through the conduit 33*a* to be smoothly performed accordingly, and allows the treatment instrument 20 to be stably held at least in the vicinity of the distal end portion of the insertion section 9.

As described above, according to the one embodiment described above, the treatment instrument 20 can stably be inserted through the conduit 33*a* in the case of using the conduit 33*a* as the treatment instrument insertion channel by adopting the configuration in which the two projecting portions (35*a*, 35*b*) are provided on the inner surface of the conduit 33*a*.

In the case of performing a predetermined treatment using the treatment instrument 20, the treatment instrument 20 can be stably held by the respective projecting portions (35*a*, 35*b*), which can contribute to improvement of the operability of the treatment instrument 20.

Further, by providing the two recessed portions (36*a*, 36*b*) at positions (surface) respectively facing the two projecting portions (35*a*, 35*b*) to configure the inner diameter of the conduit 33*a* in the direction perpendicular to the longitudinal axis to be always substantially identical, the suction force for suction targets can be prevented from being reduced in the case where the conduit 33*a* as the treatment instrument insertion channel is used as the suction conduit as well.

Note that in the one embodiment described above, the conduit 33*a* includes also the conduit in the distal end portion 6. Therefore, a configuration may be adopted in which the two projecting portions (35*a*, 35*b*) provided in the conduit 33*a* are provided on the inner surface of the conduit formed integrally with the multi-lumen tube constituting the insertion section 9, or a configuration may be adopted in which the two projecting portions (35*a*, 35*b*) are provided on the inner surface of the conduit in the distal end portion 6, for example.

As the plurality of projecting portions (35*a*, 35*b*) provided in the conduit 33*a*, at least two projecting portions (35*a*, 35*b*) should only be provided at predetermined positions at least in the vicinity of the distal end portion of the insertion section 9.

Thus, the one embodiment described above has shown the configuration example in which the two projecting portions (35*a*, 35*b*) are provided in the vicinity of the distal end portion of the insertion section 9 on the inner surface of the conduit 33*a*. However, the present disclosure is not limited to the configuration example.

For example, in addition to the configuration example shown in the one embodiment described above, a configuration may be adopted in which a plurality of projecting portions are continuously provided in a staggered manner from a position in the vicinity of the distal end portion of the conduit 33*a* toward the proximal end side in the longitudinal direction.

Alternatively, in addition to the configuration example (at the distal end position) shown in the one embodiment described above, a configuration may be adopted in which a plurality of sets of at least two projecting portions (35*a*, 35*b*), for example, are provided at predetermined intervals in the longitudinal direction of the conduit 33*a*.

Further, in addition to the configuration example (at the distal end position) shown in the one embodiment described above, a configuration may be adopted in which projecting portions are provided as appropriate at predetermined positions such as an intermediate position of the conduit 33*a* and a position closer to the proximal end of the conduit 33*a*.

By adopting each of these configurations, a smoother and stable insertion property can further be ensured when allowing insertion of the treatment instrument 20 through the conduit 33*a* without causing flection or the like of the treatment instrument 20.

Although the one embodiment described above has shown the configuration example in which the plurality of (two) projecting portions (35*a*, 35*b*) are provided on the inner surface of the conduit 33*a*, the present disclosure is not limited to the configuration example.

For example, the first projecting portion 35*a*, the second projecting portion 35*b*, the first recessed portion 36*a*, and the second recessed portion 36*b* can also be formed by forming the inner surface of the conduit into a corrugated shape or a helical shape.

Figure 5:
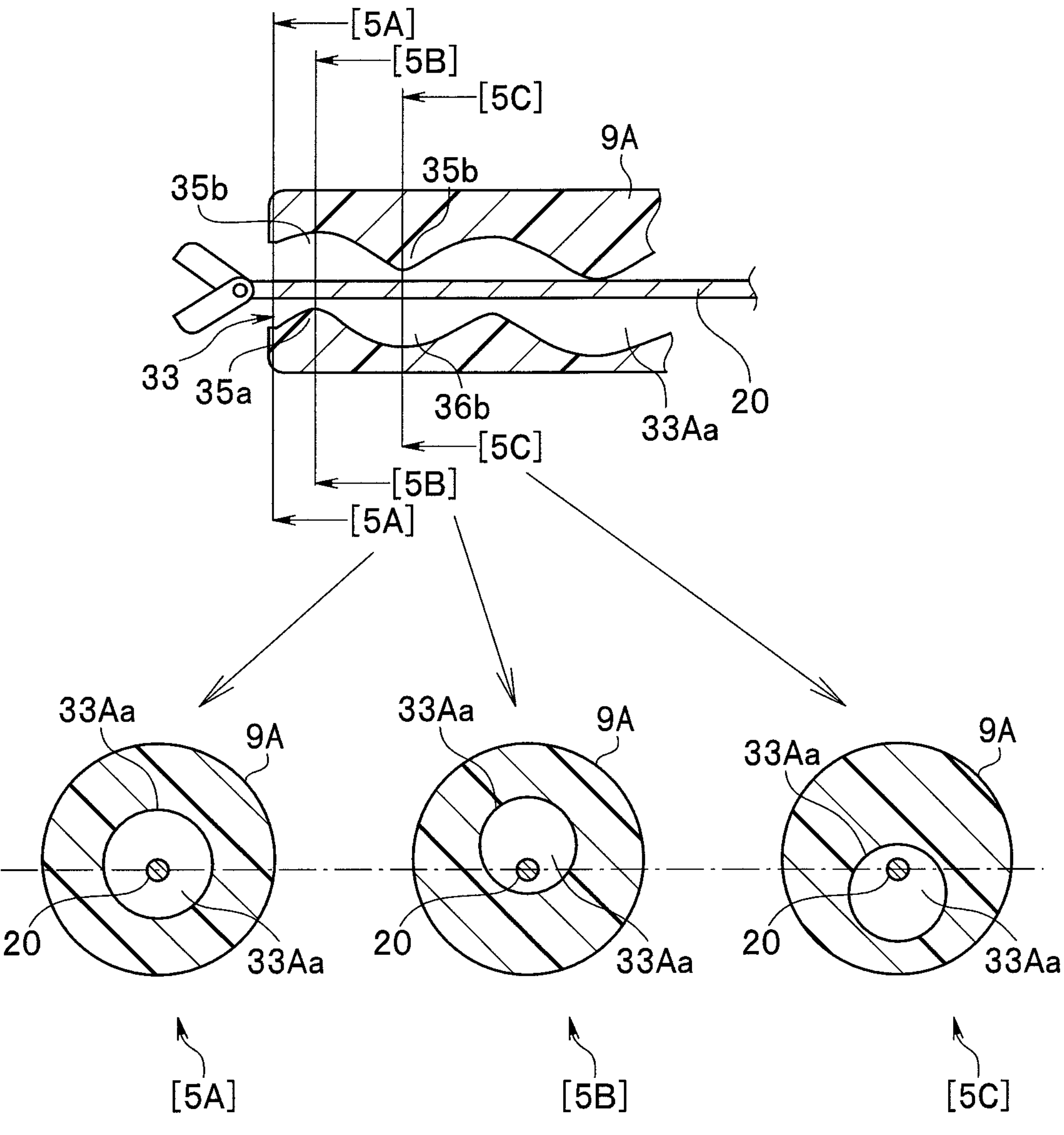
FIG. 5 is a diagram showing a first modification of a conduit configuration of the embodiment of the present disclosure.

Herein, FIG. 5 is a diagram showing a first modification of the conduit configuration of the one embodiment of the present disclosure. FIG. 5 shows an example in the case where the inner surface of a conduit 33Aa is formed into a corrugated shape. Note that in FIG. 5, reference characters [5A], [5B], and [5C] are notations in conformity with the reference characters [3A], [3B], and [3C] in FIG. 3.

In the first modification, the first projecting portion 35*a*, the second projecting portion 35*b*, the first recessed portion 36*a*, and the second recessed portion 36*b* are continuously formed by forming the inner surface of the conduit 33Aa provided in an insertion section 9A into a corrugated shape. The configuration including the positions, shapes, and the like of the first projecting portion 35*a*, the second projecting portion 35*b*, the first recessed portion 36*a*, and the second recessed portion 36*b* in this case is substantially the same as the configuration of the one embodiment described above. The inner surface of the conduit 33Aa has the corrugated shape including a plurality of ridges and a plurality of valleys. The plurality of ridges includes the first projecting portion 35*a* and the second projecting portion 35*b* and the plurality of valleys includes the first recessed portion 36*a* and the second recessed portion 36*b*. The inner surface of the conduit 33Aa has a helical shape including a helical ridge and a helical valley. The helical shape extends in the longitudinal direction of the insertion section 9. The helical ridge forms the first projecting portion 35*a* and the second projecting portion 35*b* and the helical valley forms the first recessed portion 36*a* and the second recessed portion 36*b*.

By adopting such a configuration, the inner surface of the conduit 33Aa can be formed as a continuous surface. Therefore, the configuration can ensure a more stable and smooth insertion property when allowing insertion of the treatment instrument 20 through the conduit 33Aa having a large diameter. At the same time, when suction targets are suctioned using the conduit 33Aa, the configuration can prevent the suction targets from being jammed in the conduit 33Aa even if solidified residues, for example, are included in the suction targets, and can prevent the suction force for the suction targets from being reduced to ensure an always smooth suctioning property.

Figure 6:
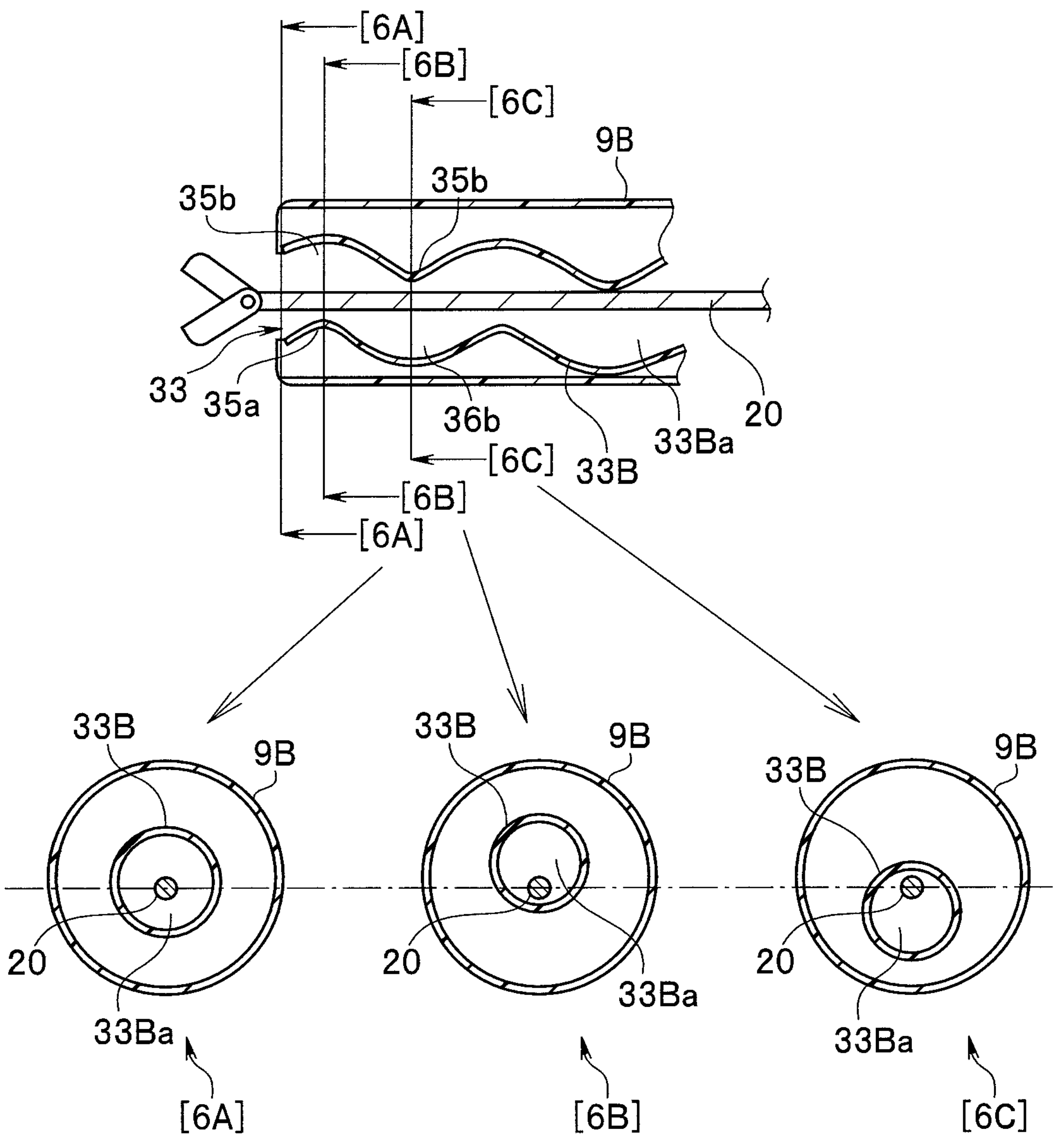
FIG. 6 is a diagram showing a second modification of the conduit configuration of the embodiment of the present disclosure.

The present disclosure can also be applied to an endoscope in a form configured by allowing insertion of a separate channel tube (conduit) through a tube-like member constituting the insertion section, for example. FIG. 6 is a diagram showing a second modification of the conduit configuration of the one embodiment of the present disclosure. FIG. 6 shows an example in a case where a channel tube 33B forming a conduit 33Ba is disposed in an insertion section 9B in a meandering manner. Note that in FIG. 6, reference characters [6A], [6B], and [6C] are notations in conformity with the reference characters [3A], [3B], and [3C] in FIG. 3.

In the second modification, at least two projecting portions (35*a*, 35*b*) and two recessed portions (36*a*, 36*b*) corresponding to the two projecting portions are continuously formed in the conduit 33Ba by disposing the channel tube 33B provided in the insertion section 9B in a meandering manner. The configuration including the positions, shapes, and the like of the first projecting portion 35*a*, the second projecting portion 35*b*, the first recessed portion 36*a*, and the second recessed portion 36*b* in this case is substantially the same as the configuration of the one embodiment described above. Note that the configuration example shown in FIG. 6 illustrates a configuration in which not only the two projecting portions and the two recessed portions, but also projecting portions and recessed portions are further continuously provided.

By adopting such a configuration, the configuration of the present disclosure can be applied even to the endoscope in the form configured by allowing insertion of a separate channel tube (conduit) through the insertion section, similarly to the one embodiment and the first modification described above, and substantially the same effects can be obtained.

In addition, with the configuration of the second modification, the configuration in which at least two projecting portions (35*a*, 35*b*) and two recessed portions (36*a*, 36*b*) corresponding to the two projecting portions are formed utilizing the channel tube as the conduit is adopted, which can eliminate the process the channel tube 33B (the conduit 33Ba) itself. Therefore, the manufacturing process can be simplified, thus enabling contribution to reduction of manufacturing cost.

The projecting portions provided on the inner surface of the conduit in the one embodiment described above can also be configured in a form as shown in each of the following modifications.

Figure 7:
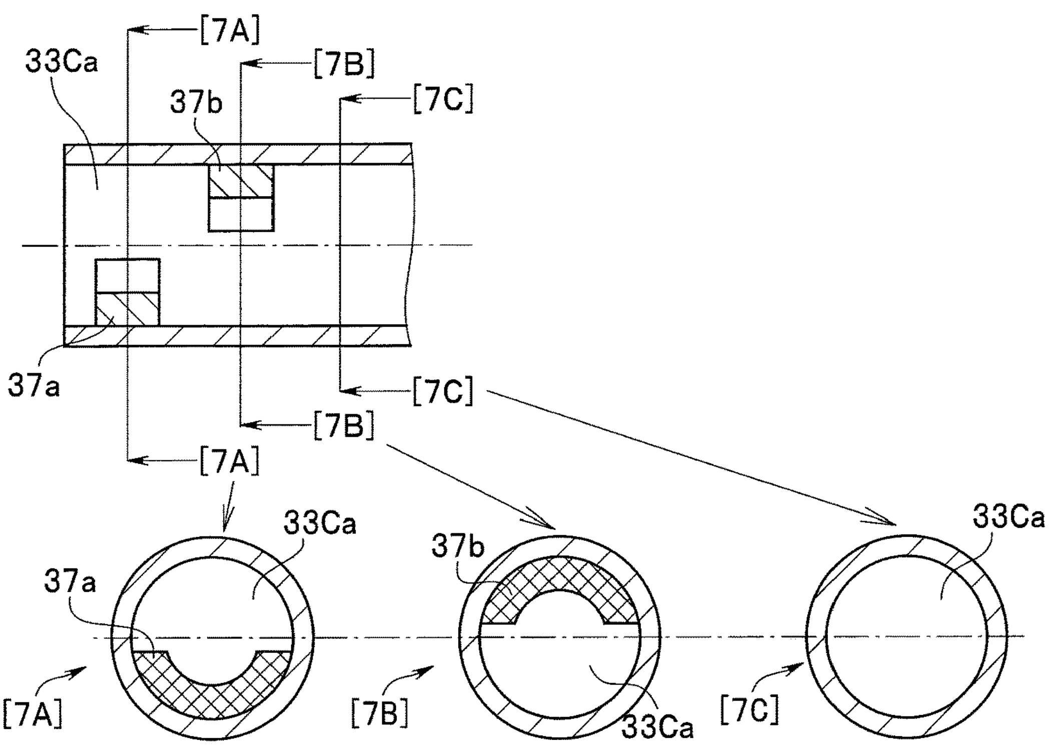
FIG. 7 is a diagram showing a third modification of the conduit configuration of the embodiment of the present disclosure.

First, FIG. 7 is a diagram showing a third modification of the conduit configuration of the one embodiment of the present disclosure. Note that in FIG. 7, reference characters [7A], [7B], and [7C] are notations in conformity with the reference characters [3A], [3B], and [3C] in FIG. 3.

In the third modification, a component permeable to liquid is provided on the inner surface of a channel tube as a conduit 33Ca, thus forming a first projecting portion 37*a* and a second projecting portion 37*b*. Note that in the case of the configuration, recessed portions corresponding to the two projecting portions (37*a*, 37*b*) are not provided. The first projecting portion 37*a* and the second projecting portion 37*b* are configured to allow passing fluid in the longitudinal direction.

The third modification in FIG. 7 shows a configuration example in which the two projecting portions (37*a*, 37*b*) provided on the inner surface of the conduit 33Ca are formed of mesh members, for example, as an example of the component permeable to liquid. Herein, each of the two projecting portions (37*a*, 37*b*) formed of the mesh members is provided within a predetermined range (substantially half of the perimeter) in the circumferential direction on the inner surface of the conduit 33Ca as shown in FIG. 7, for example. In this case, the first projecting portion 37*a* and the second projecting portion 37*b* are provided at positions axially symmetric to each other around the central axis Ax of the conduit 33Ca. The mesh members are bonded to the inner surface of the conduit 33Ca using an adhesive material, for example. At least one of the first projecting portion 37*a* and the second projecting portion 37*b* include a liquid permeable portion. The first projecting portion 38*a* includes a first plurality of plates on a first circumferential portion of the inner surface of the conduit 33Da, and a plane of each plate of the first plurality of plates is oriented radially and in the longitudinal direction.

Figure 8:
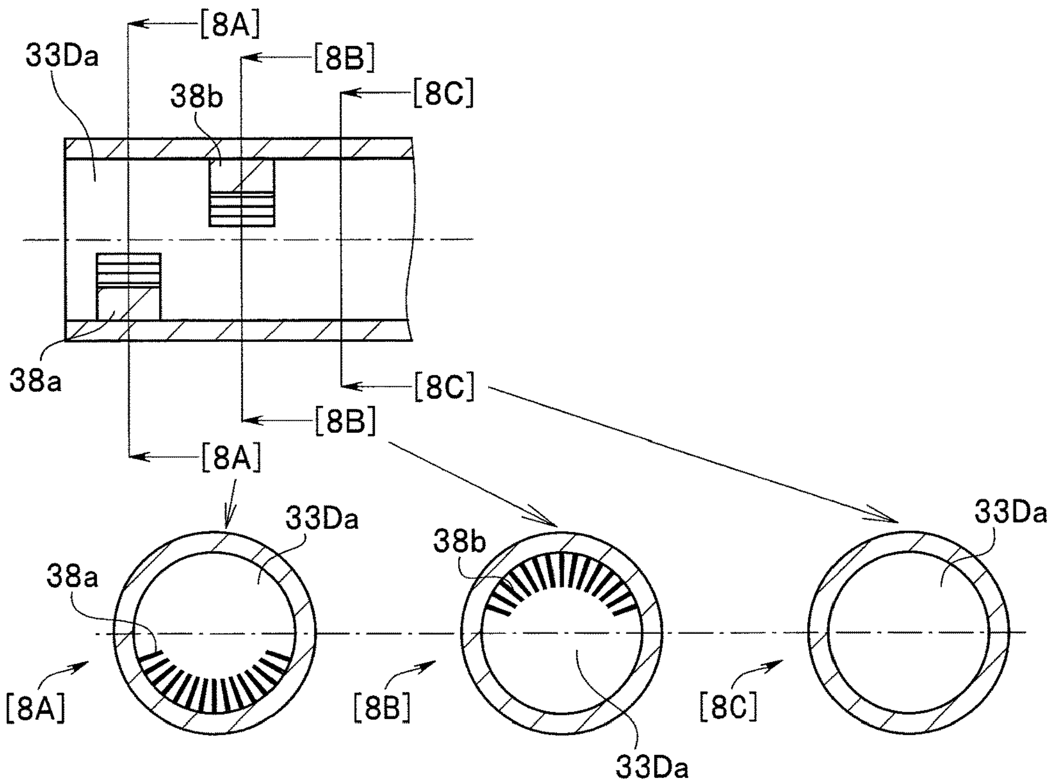
FIG. 8 is a diagram showing a fourth modification of the conduit configuration of the embodiment of the present disclosure.

FIG. 8 is a diagram showing a fourth modification of the conduit configuration of the one embodiment of the present disclosure. Note that in FIG. 8, reference characters [8A], [8B], and [8C] are notations in conformity with the reference characters [3A], [3B], and [3C] in FIG. 3.

In the fourth modification, a plurality of plate-like members, for example, are arranged side by side in a predetermined form on the inner surface of a channel tube as a conduit 33Da as another illustration of the component permeable to liquid, thus forming a first projecting portion 38*a* and a second projecting portion 38*b*.

Herein, each of the two projecting portions (38*a*, 38*b*) has a form in which a plurality of plate-like members arranged parallel to a plane parallel to the longitudinal axis are arranged side by side at predetermined intervals within a predetermined range (substantially half of the perimeter) in the circumferential direction on the inner surface of the conduit 33Da. In this case, the first projecting portion 38*a* and the second projecting portion 38*b* are provided at positions axially symmetric to each other around the central axis Ax of the conduit 33Da. The plurality of plate-like members are bonded to the inner surface of the conduit 33Da using an adhesive material, for example. Note that also in the case of the configuration, recessed portions corresponding to the two projecting portions (38*a*, 38*b*) are not provided. The second projecting portion 38*b* includes a second plurality of plates on a second circumferential portion of the inner surface of the conduit 33Da, and a plane of each plate of the second plurality of plates is oriented radially and in the longitudinal direction. The first projecting portion 38*a* includes a first plurality of rod-like members on a first circumferential portion of the inner surface of the conduit 33Da. The second projecting portion 38*b* includes a second plurality of rod-like members on a second circumferential portion of the inner surface of the conduit.

Note that the above-described fourth modification can also be modified and configured in the following manner. In other words, the first projecting portion and the second projecting portion may be formed of a plurality of rod-like members (not shown), for example. In the case of the configuration, a plurality of rod-like members are arranged side by side at predetermined intervals within a predetermined range in the longitudinal direction on the inner surface of the conduit, and a plurality of rod-like members are arranged side by side at predetermined intervals within a predetermined range in the circumferential direction. In other words, a plurality of rod-like members are used and provided in a brush shape in a predetermined region of the inner surface of the conduit, thus forming the two projecting portions. Also in this case, recessed portions are not required.

In the third and fourth modifications configured in this manner, the two projecting portions are formed of components permeable to liquid. Thus, suctioning is not affected by the projecting portions. Therefore, the suction force for suction targets can be prevented from being reduced at the time of suctioning without providing recessed portions to ensure the inner diameter of the conduit. Therefore, the step of forming recessed portions can be omitted accordingly in the manufacturing process, which can contribute to reduction of manufacturing cost.

Note that the configurations of the above-described third and fourth modifications are not limited to the above-described configuration examples, but can also be applied absolutely similarly to the inner surface of a conduit formed integrally with a multi-lumen tube.

Figure 9:
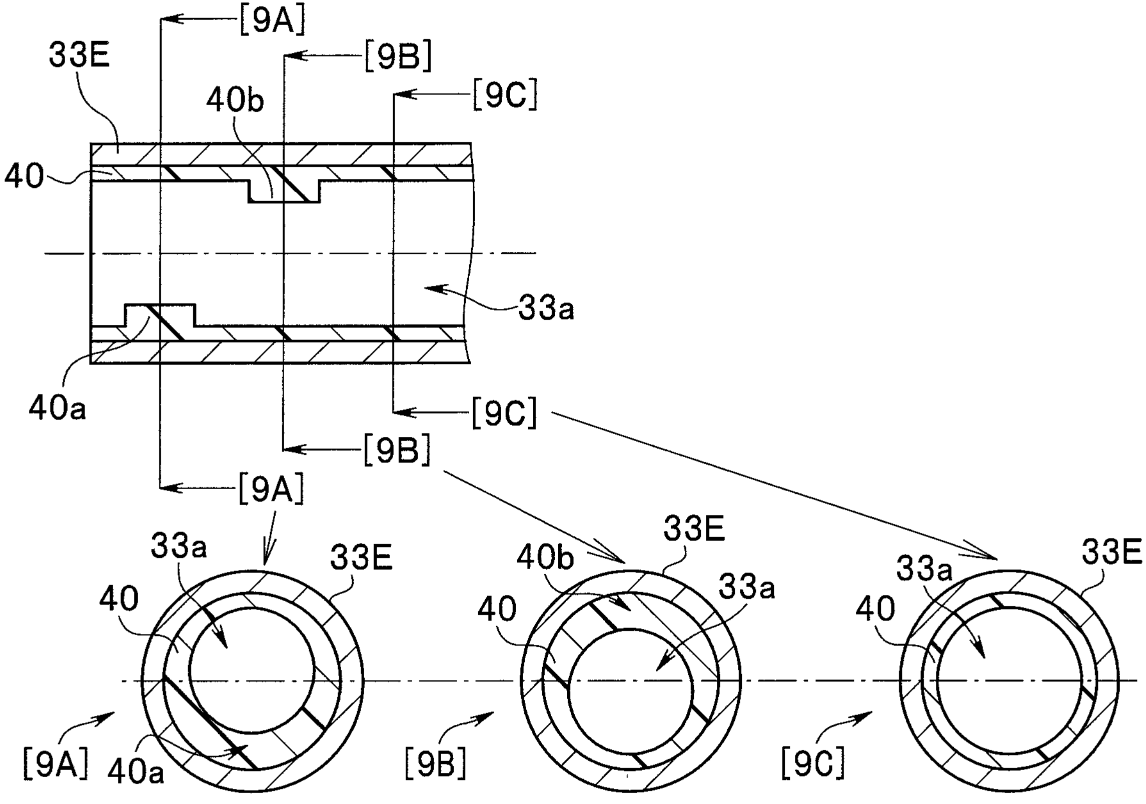
FIG. 9 is a diagram showing a fifth modification of the conduit configuration of the embodiment of the present disclosure.

FIG. 9 is a diagram showing a fifth modification of the conduit configuration of the one embodiment of the present disclosure. Note that in FIG. 9, reference characters [9A], [9B], and [9C] are notations in conformity with the reference characters [3A], [3B], and [3C] in FIG. 3.

The fifth modification is an illustration of a conduit configured by providing an attachable/detachable sheath 40 in a channel tube 33E. In the case of the configuration, an inner region of the sheath 40 functions as the conduit 33*a*. Thus, a first projecting portion 40*a* and a second projecting portion 40*b* are formed on the inner surface of the sheath 40 in the fifth modification. In this case, the two projecting portions (40*a*, 40*b*) may be formed integrally with the sheath 40, or may have a form in which the component in the form shown in the above-described third or fourth modification is provided by adhesion or the like. Note that the configuration example shown in FIG. 9 shows an example in which recessed portions are omitted. However, the fifth modification is not limited to the form of FIG. 9. Therefore, the fifth modification may be configured as a form in which recessed portions are provided, in addition to the configuration example of FIG. 9, for example. The conduit is formed of the sheath 40, and the inner surface of the sheath 40 is the inner surface of the conduit. The insertion section 9 includes the channel tube 33E and the sheath 40 is reversibly attached to an inner surface of the channel tube 33E.

The fifth modification having such a configuration may perform preparation of the sheath 40 separate from the endoscope, and may eliminate the process the treatment instrument insertion channel (conduit) itself in the insertion section of the endoscope. It is therefore possible to contribute to reduction of manufacturing cost.

By attaching the sheath 40 to the treatment instrument insertion channel when the treatment instrument is used, the operability of the treatment instrument can be improved. At the time of suctioning, the sheath 40 is detached from the treatment instrument insertion channel to enable suctioning to be performed through the conduit having a large diameter without reducing the suction force for suction targets.

It goes without saying that the present disclosure is not limited to the above-described embodiment, but various modifications and applications can be carried out within a range not departing from the gist of the disclosure. Further, the above-described embodiment includes disclosures in various stages, and various disclosures may be extracted by appropriate combinations in a plurality of configuration as disclosed. For example, even if some configurations are removed from all of the configurations shown in the one embodiment described above, and a configuration from which the configurations have been removed may be extracted as a disclosure in a case where the problems to be solved by the disclosure can be solved and effects of the disclosure are obtained. Furthermore, constitutional elements according to different embodiments may be combined as appropriate. The present disclosure is not restricted by a specific embodiment of the disclosure except being limited by the appended claims.

Example 1

An endoscope comprising:
- an insertion section;
- a conduit provided in the insertion section;
- a first projecting portion provided on an inner surface of the conduit; and
- a second projecting portion provided on the inner surface of the conduit at a position different from a position of the first projecting portion in a direction of a longitudinal axis of the insertion section and at a position different from a position of the first projecting portion in a circumferential direction around the longitudinal axis.

Example 2

The endoscope according to Example 1, wherein the first projecting portion and the second projecting portion are provided axially symmetric to each other around a central axis of the conduit.

Example 3

The endoscope according to Example 1, comprising:
- a first recessed portion provided on a surface facing the first projecting portion on the inner surface of the conduit; and
- a second recessed portion provided on a surface facing the second projecting portion on the inner surface of the conduit.

Example 4

The endoscope according to Example 3, wherein the first projecting portion, the second projecting portion, the first recessed portion, and the second recessed portion are formed by forming the inner surface of the conduit into a corrugated shape.

Example 5

The endoscope according to Example 3, wherein the first projecting portion, the second projecting portion, the first recessed portion, and the second recessed portion are formed by forming the inner surface of the conduit into a helical shape.

Example 6

The endoscope according to Example 1, wherein a top part of the first projecting portion and a top part of the second projecting portion have an interval larger than or equal to a maximum outer diameter of a treatment instrument inserted in the conduit in a direction perpendicular to the longitudinal axis.

Example 7

The endoscope according to Example 1, wherein assuming that in the direction of the longitudinal axis, a position at which the first projecting portion is provided is a first position, a position at which the second projecting portion is provided is a second position, and a position different from the first position and the second position is a third position, a shortest distance between the first projecting portion and the second projecting portion is larger than or equal to an inner diameter of the conduit at the third position.

Example 8

The endoscope according to Example 3, wherein
- the conduit is a channel tube disposed in the insertion section in a meandering manner, and
- the first projecting portion, the second projecting portion, the first recessed portion, and the second recessed portion are formed by meandering of the channel tube.

Example 9

The endoscope according to Example 1, wherein the first projecting portion and the second projecting portion are configured to be permeable to liquid.

Example 10

The endoscope according to Example 9, wherein the first projecting portion and the second projecting portion are formed of mesh members.

Example 11

The endoscope according to Example 9, wherein
- the first projecting portion and the second projecting portion are formed of a plurality of plate-like members, and
- the plurality of plate-like members are arranged side by side with each plate surface being directed in a direction along the longitudinal axis on an inner circumferential surface of the conduit and at predetermined intervals within a predetermined range in the circumferential direction.

Example 12

The endoscope according to Example 9, wherein
- the first projecting portion and the second projecting portion are formed of a plurality of rod-like members, and
- on an inner circumferential surface of the conduit, the plurality of rod-like members are arranged side by side at predetermined intervals within a predetermined range in the direction of the longitudinal axis, and are arranged side by side at predetermined intervals within a predetermined range in the circumferential direction.

Example 13

The endoscope according to Example 1, further comprising a sheath which is attachable/detachable in the conduit, wherein
- the inner surface of the conduit is an inner surface of the sheath, and the first projecting portion and the second projecting portion are provided on the inner surface of the sheath.

What is claimed is:

1. An endoscope, comprising:

an insertion section including a conduit having a continuous inner surface, an inner diameter, and a longitudinal center axis, and, wherein the inner surface at a distal end of the insertion section comprises:

a first projection provided at a first position, a second projection provided at a second position, and a first recess provided at a third position, wherein, in a longitudinal direction of the insertion section, the first position is different from the second position, wherein, in a direction perpendicular to the longitudinal center axis:

a distance from the radially innermost surface of the first projection to a radially outermost surface of the first recess is a first distance, wherein the first distance is the same as the inner diameter of the conduit, wherein the inner surface at the distal end of the insertion section further comprises:

a second recess provided at a fourth position, wherein, in the longitudinal direction of the insertion section, the first position is the same as the third position, wherein, in the longitudinal direction of the insertion section, the fourth position is the same as the second position, wherein, in a side cross-sectional view and relative to a baseline surface of the conduit:

the first projection and the second projection are each protruded from the baseline surface, and the first recess and the second recess are each recessed from the baseline surface, and wherein, in the side cross-sectional view, the first recess faces the first projection and the second recess faces the second projection.

2. The endoscope according to claim 1, wherein, in a circumferential direction of the insertion section, the first position is different from the second position.

3. The endoscope according to claim 1, wherein the first projection is provided on a first inner surface portion and the second projection is provided on a second inner surface portion, and wherein, in a side cross-sectional view, the first inner surface portion is on a first side of the longitudinal center axis of the insertion section and the second inner surface portion is on a second side of the longitudinal center axis of the insertion section.

4. The endoscope according to claim 3, wherein the first recess is on the second side of the longitudinal center axis of the insertion section and facing the first projection.

5. The endoscope according to claim 4, wherein the first projection includes a first projecting side wall surface, wherein the first recess includes a first recessed side wall surface and a bottom surface, wherein the first projecting side wall surface intersects a baseline surface of the conduit at a first obtuse angle, and wherein the first recessed side wall surface intersects the bottom surface at a second obtuse angle.

6. The endoscope according to claim 1, wherein the inner surface at the distal end of the insertion section of the conduit has a corrugated shape including a plurality of ridges and a plurality of valleys, and wherein the plurality of ridges includes the first projection and the second projection and the plurality of valleys includes the first recess and the second recess.

7. The endoscope according to claim 1, wherein the inner surface at the distal end of the insertion section of the conduit has a helical shape including a helical ridge and a helical valley, wherein the helical shape extends in the longitudinal direction of the insertion section, and wherein the helical ridge forms the first projection and the second projection and the helical valley forms the first recess and the second recess.

8. The endoscope according to claim 1, wherein the first projection has a first height in a radial direction of the conduit, wherein the second projection has a second height in the radial direction of the conduit, and wherein the first height and the second height are less than a radius of the conduit.

9. The endoscope according to claim 1, wherein a shortest distance between the first projection and the second projection defines a projection separation distance, and wherein the projection separation distance is larger than the inner diameter of the conduit.

10. The endoscope according to claim 1, wherein the conduit is formed of a sheath, wherein an inner surface of the sheath is the continuous inner surface of the conduit, and wherein the insertion section includes a channel tube and the sheath is reversibly attached to an inner surface of the channel tube.

11. The endoscope according to claim 1, wherein in an axial view in a direction along the longitudinal center axis of the conduit:

the first projection and the first recess form a first circular cross section, the second projection and the second recess form a second circular cross section, the baseline surface forms a third circular cross section, the first circular cross section, the second circular cross section, and the third circular cross sections have substantially same diameters.

12. The endoscope according to claim 1, wherein, in a direction perpendicular to the longitudinal center axis: a distance from the longitudinal center axis to a radially innermost surface of the first projection is a second distance, and a distance from the longitudinal center axis to a radially innermost surface of the second projection is a third distance, and wherein the second distance is the same as the third distance.

13. The endoscope according to claim 12, wherein, in the direction perpendicular to the longitudinal center axis, a distance from the radially innermost surface of the second projection to a radially outermost surface of the second recess is a fourth distance, and wherein the first distance is the same as the fourth distance.

* * * * *